United States Patent [19]

Stringfield

[11] Patent Number: 4,632,560
[45] Date of Patent: Dec. 30, 1986

[54] METHOD AND APPARATUS FOR IMPROVED INSPECTION OF CONTINUOUS WEBS

[76] Inventor: Horace C. Stringfield, 110 Lakeside Ave., Pompton Lakes, N.J. 07442

[21] Appl. No.: 823,079

[22] Filed: Jan. 27, 1986

Related U.S. Application Data

[63] Continuation of Ser. No. 602,737, Apr. 23, 1984, abandoned.

[51] Int. Cl.⁴ ............................................. G01N 21/84
[52] U.S. Cl. ..................................................... 356/431
[58] Field of Search ........................................... 356/431

Primary Examiner—Bernard D. Pianalto
Attorney, Agent, or Firm—Morgan & Finnegan

[57] ABSTRACT

An improved method and apparatus is disclosed for the inspection of continuous running webs such as those used in the printing trade. A rotating drum of mirrors, having a polygonal cross-section, allows inspection of a repeating image on the web, such that the repeating image on the moving web appears stationary to the viewer. The target portion of the web is oriented with respect to the rotating drum so that a straight line bisecting the target portion of the web passes through a locus of points having as its center the point halfway between the center of the drum and the viewing point on the drum. The sweeping scanning angle continually maintains correspondence to one repeat length of the web.

9 Claims, 6 Drawing Figures

METHOD AND APPARATUS FOR IMPROVED INSPECTION OF CONTINUOUS WEBS

This is a continuation of application Ser. No. 602,737, filed Apr. 23, 1984, now abandoned.

BACKGROUND OF THE INVENTION

The invention relates to methods and apparatus for the inspection of repeating patterns or designs on a moving web.

More specifically, the invention relates to inspection methods and apparatus wherein mirrors are mounted on a rotary drum of polygonal cross-section, a single mirror being mounted on each distinct outer side of the drum. Methods and apparatus of this type are described in U.S. Pat. No. 3,089,381 issued to Bogert.

In prior art rotary drum mirror methods and apparatus, the target web has customarily been positioned so that it is bisected by a line passing through the viewing point, i.e., the central point on the drum at which a viewing telescope is usually aimed. In prior art rotating mirror drum methods and apparatus, there were often provided 20 mirrors, one on each of 20 outer faces of the drum. In such systems, normally the web consisted of two straight sections which met to form an angle of approximately 162 degrees, said web angle facing and being aligned with the central viewing point of the 20 mirror rotating drum.

Although prior art mirror rotary drum web inspection systems have been in use for some time, they have not proved entirely satisfactory. One particularly serious problem associated with their operation has long been taken for granted. This is the problem known as the separation of image problem or the extraneous web image problem. In such systems, when one mirror and only one fills the viewing area at one instant, the image will appear to be steady and clear to the viewer. However, in commercial systems of the prior art, extraneous images appear to the viewer as a result of the rotation of the mirrors and the concomitant intrusion into the viewing area of secondary mirror images. There has been no way up until now to control these extraneous images. For instance, oscillating mirrors, often located between the telescope sight line and the rotary prism, can only correct the images on the primary mirror through which the web is sighted. The extraneous images produced on a secondary mirror within the viewing area cannot receive the proper correction. This results in image movement or separation of two partial images which should be superimposed. The extraneous web images produced can lead to costly inspection errors as well as to viewer fatigue and uncertainty, and also restrict the speed at which the target web can move and still be reliably inspected.

One proposed solution to the problem has been to baffle off areas of the target web to prevent the viewing of extraneous images. However, this is undesirable because it necessarily restricts the portion of the moving target web that can be inspected at any given instant. This sometimes results in inspection error. Also, baffling can sometimes introduce confusing interruptions of images in the viewing area.

It is, therefore, an object of the invention to improve rotary prism web systems by providing methods and apparatus which will correct the extraneous image problem without the use of baffles.

It is a further object of the invention to provide methods and apparatus wherein the sweeping scanning angle continuously maintains correspondence to one repeat length of the web so that the viewing image presented to the viewer by the primary and secondary mirrors are coincident.

It is a further ooject of the invention to provide methods and apparatus for the inspection of repeating patterns of designs on a moving web which can operate reliably at moving web speeds of up to at least 1800 feet per minute without any separation of image problem.

SUMMARY OF THE INVENTION

The invention comprises improved methods and apparatus for the inspection of continuous running webs, such as those used in the printing trade, wherein a rotating drum of mirrors, having a polygonal cross-section, rotates in time sequence with the moving web so as to allow inspection of the repeating image on the web such that the repeating image on the moving web appears stationary to the viewer. In such methods and apparatus of the present invention, the target portion of the web is oriented with respect to the rotating drum so that a straight line bisecting the target portion of the web passes through a locus of points having as its center a point halfway between the center of the drum and the viewing point on the drum. The sweeping scanning angle thereby continuously maintains correspondence to one repeat length of the web.

DETAILED DESCRIPTION OF THE DRAWINGS

Figure 1:
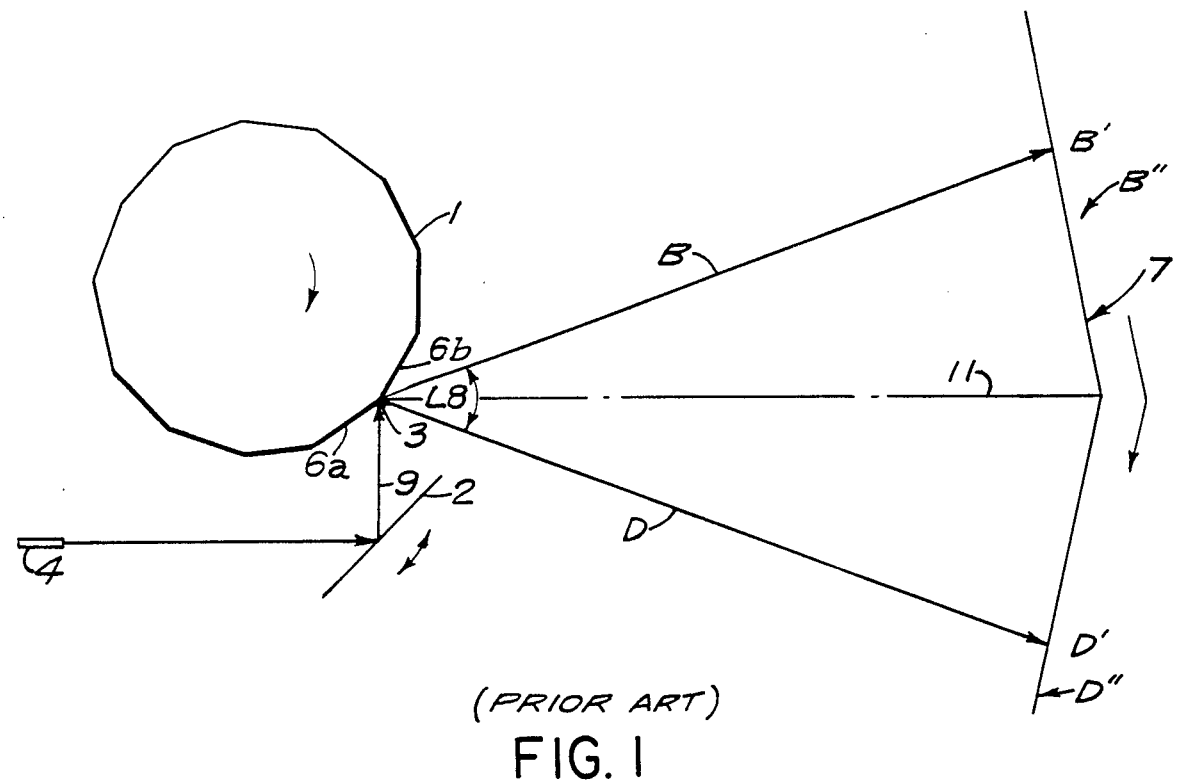
FIG. 1 illustrates a rotary prism scanning device of the prior art which is in widespread use.

Referring first to the prior art system of FIG. 1, rotary prism 1 comprises a drum of polygonal cross-section wherein upon each outer side of the polygon is mounted a mirror. The rotary prism is adapted for rotation in a clockwise direction, as is depicted by the arrow. As the prism rotates, there is a point 3 which is sighted by a viewer through telescope 4 and oscillating mirror 2. As is well known to those of skill in the art, the image which appears to the viewer through the telescope is essentially that portion of the target web 7, to which sight lines B and D, from mirrors 6b and 6a, respectively are directed.

Consider that the viewing area on the rotary prism, i.e., which includes the point 3, is completely filled by a single mirror at only one instant, e.g., when point 3 falls in the center of rotating mirror 6a. At all other times there is an extraneous partial image produced on a portion of a second rotating mirror which intrudes into the viewing area. For instance, in FIG. 1 at the position of the rotary prism shown, each of mirrors 6a and 6b produce an image to the viewer (i.e., the images on the target web at the end of sight lines D and B). Some viewing corrections, i.e., those described in Bogert U.S. Pat. No. 3,098,381 are afforded by the oscillating mirror 2; however, such corrections operate only with respect to the one mirror through which the sight line 9 passes and have no effect with respect to the secondary mirror images.

Such prior art systems theoretically allow inspection of the target web in such a way that the repeating pattern on the web appears stationary. However, as the prism 1 rotates from the position shown in FIG. 1, the view presented by mirrors 6a and 6b will be directed toward points B" and D". The images presented from these points will be separated or not superimposed for reasons more fully described below with reference to FIGS. 5 and 6. In fact, in systems of the prior art it is only at the instant that the sweeping scanning angle 8 is centered on the target web that the sweeping scanning angle corresponds to one repeat length of the web and a single, complete image is presented to the viewer.

To further explain the inherent nature of this limitation of the prior art, note that in the embodiment shown in FIG. 1, the target web 7 is centered on the viewing point 3 of the rotary prism so that the center line 11 which bisects the sweeping scanning angle 8 passes through the center of the target web 7. This design is typical of the prior art and necessarily implies that the sweeping scanning angle 8 will correspond to one repeat length of the target web only at a single instant, the instant that the sweeping scanning angle 8 is centered on the target web. However, in prior art systems, as the prism rotates, causing the sweeping scanning angle 8 to be not centered on the target web, but rather to engulf points B" and D", a viewer will see partial images in mirrors 6a and 6b. Hence the separated image problem is intrinsic to the design of the prior art systems illustrated in FIG. 1. This problem will be described more fully below with reference to FIGS. 5 and 6.

Figure 2:
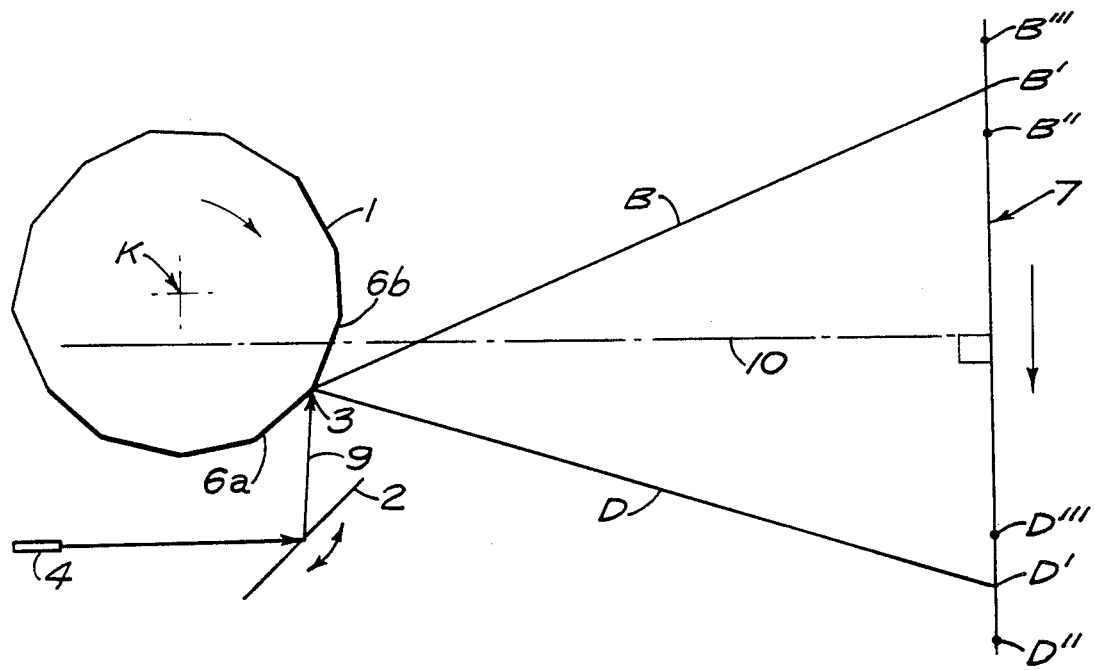
FIG. 2 is a diagram illustrating an embodiment of the present invention wherein the target web is along a straight path.

FIG. 2 illustrates one aspect of the invention, namely, the positioning of the target web 7, so that it is bisected by line 10, not the center line 11 (not shown) which passed through the viewing point 3 in the prior art. Line 10 is defined as follows: it is a line that passes through, i.e., bisects, the center of the target web and also the point halfway between rotary prism viewing point 3 and the center point K of the rotary prism 1.

In this embodiment, the sweeping scanning angle continues to correspond to one repeat length of the target web in small incremental distances above and below the points B' and D' on the target web, i.e., in the regions B"—B'" and D"—D'".

Figure 3:
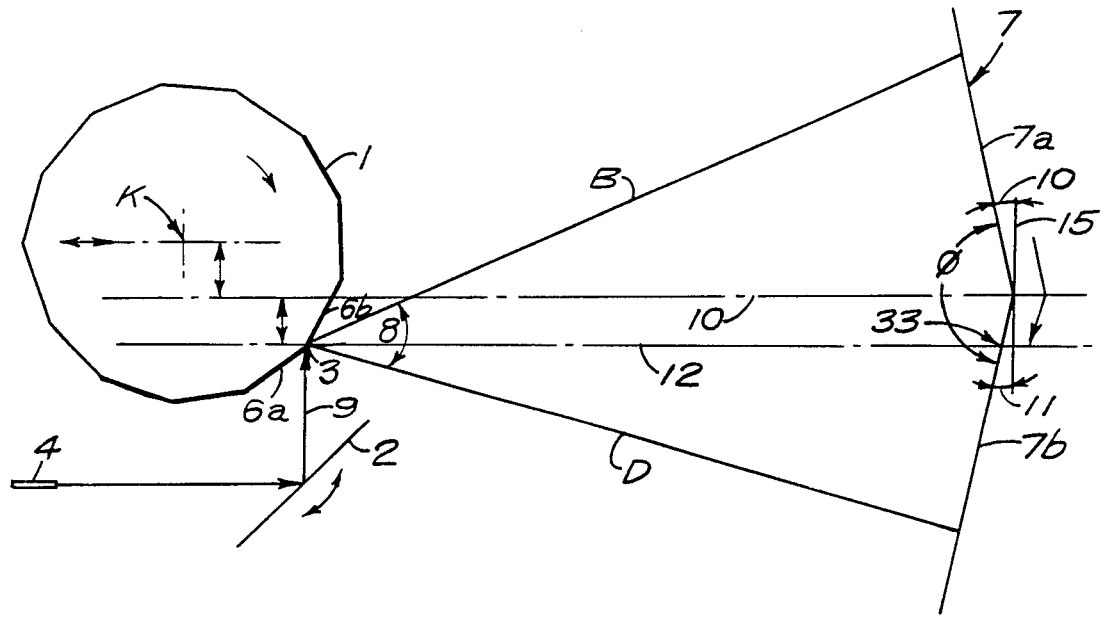
FIG. 3 is a diagram illustrating a preferred embodiment of the invention wherein the target web is bent.

In FIG. 3, a preferred embodiment of the invention wherein the target web 7 is bent, the web angle φ is bisected by a line 10 which passes through the center of the web angle and also a point halfway between the viewing point 3 and the center K of the rotary prism 1. In addition, in this embodiment, line 10 is parallel to the horizontal line, i.e., the line 12 which intersects the viewing point 3 and the point 33 directly opposite it on the target web 7.

Again referring to FIG. 3, the amplitude of the bend in the target web, represented by web angles 10 ard 11, can be determined for 20 mirror prisms based on desired web repeat lengths according to Table I.

TABLE I

| Web Repeat Lengths | Web Angles | |
|---|---|---|
| | L10 | L11 |
| 14" | 17.11° | 17.11° |
| 16" | 17.22° | 17.22° |
| 18" | 17.31° | 17.31° |
| 20" | 17.38° | 17.38° |
| 22" | 17.43° | 17.43° |
| 24" | 17.48° | 17.48° |
| 26" | 17.52° | 17.52° |
| 28" | 17.55° | 17.55° |
| 30" | 17.58° | 17.58° |
| 32" | 17.61° | 17.61° |
| 34" | 17.63° | 17.63° |
| 36" | 17.65° | 17.65° |
| 38" | 17.67° | 17.67° |
| 40" | 17.69° | 17.69° |

When the apparatus illustrated in FIG. 3 is used as indicated in Table I, the sweeping scanning angle will correspond to one web repeat length in all positions of the rotary prism 1 and thus, the separation of image problem is eliminated since mirrors 6a and 6b will at all times provide coincident images to the viewer. This improvement will be further illustrated below with reference to FIGS. 5 and 6.

Figure 4:
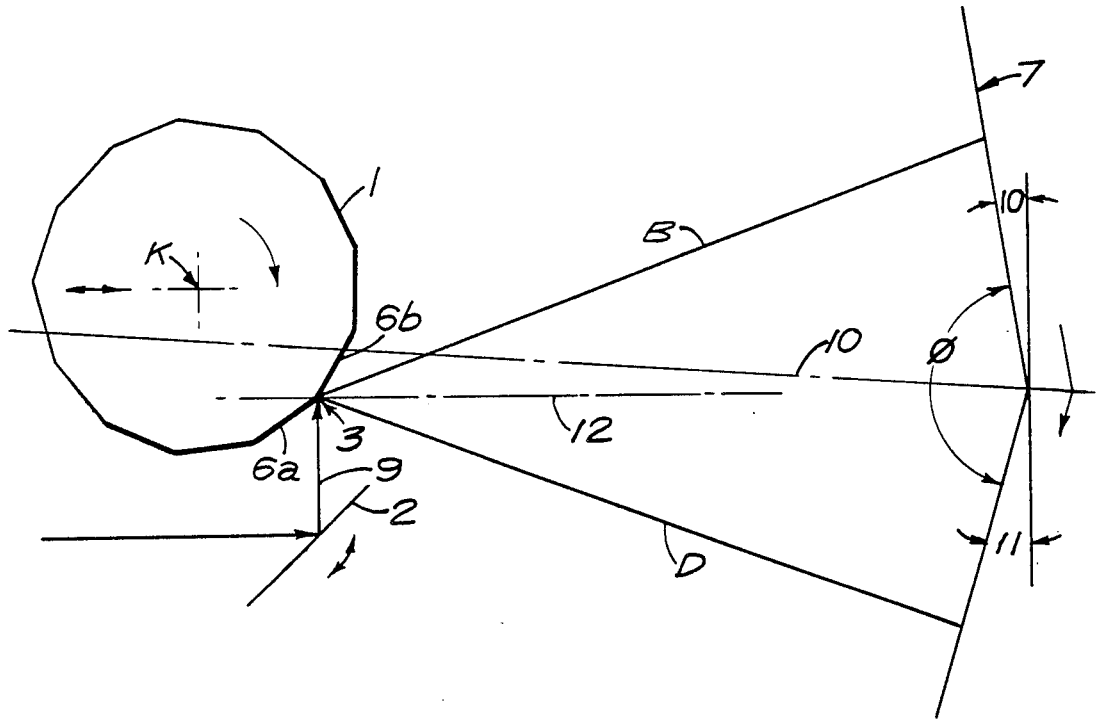
FIG. 4 is a diagram illustrating another preferred embodiment of the present invention wherein the target web is bent.

FIG. 4 shows a further preferred embodiment of the invention wherein the line 10 which bisects the web angle φ and passes through the point halfway between the rotary prism center K and the viewing point 3 is not parallel to the horizontal line, i.e., the line 12 which joins viewing point 3 and the point 33 (not shown) directly opposite it on the target web 7. In such embodiments, in order to assure that the sweeping scanning angle corresponds to one web repeat length in all viewing positions, web angles 10 and 11 should be chosen, for 20 mirror prisms, depending upon the desired web repeat length, according to Table II.

TABLE II

| Web Repeat Lengths | Web Angles | |
|---|---|---|
| | L10 | L11 |
| 14" | 13.79° | 20.43° |
| 16" | 14.31° | 20.13° |
| 18" | 14.72° | 19.84° |
| 20" | 15.05° | 19.70° |
| 22" | 15.32° | 19.55° |
| 24" | 15.54° | 19.42° |
| 26" | 15.73° | 19.31° |
| 28" | 15.89° | 19.21° |
| 30" | 16.03° | 19.13° |
| 32" | 16.16° | 19.06° |
| 34" | 16.26° | 19.00° |
| 36" | 16.36° | 18.94° |
| 38" | 16.45° | 18.89° |
| 40" | 16.53° | 18.85° |

The values in Tables I and II for web angles 10 and 11 in 20 mirror prism systems and their correspondence to target web repeating lengths have been derived empirically to assure that the sweeping scanning angle corresponds to one repeat web length in all viewing positions.

Figure 5:
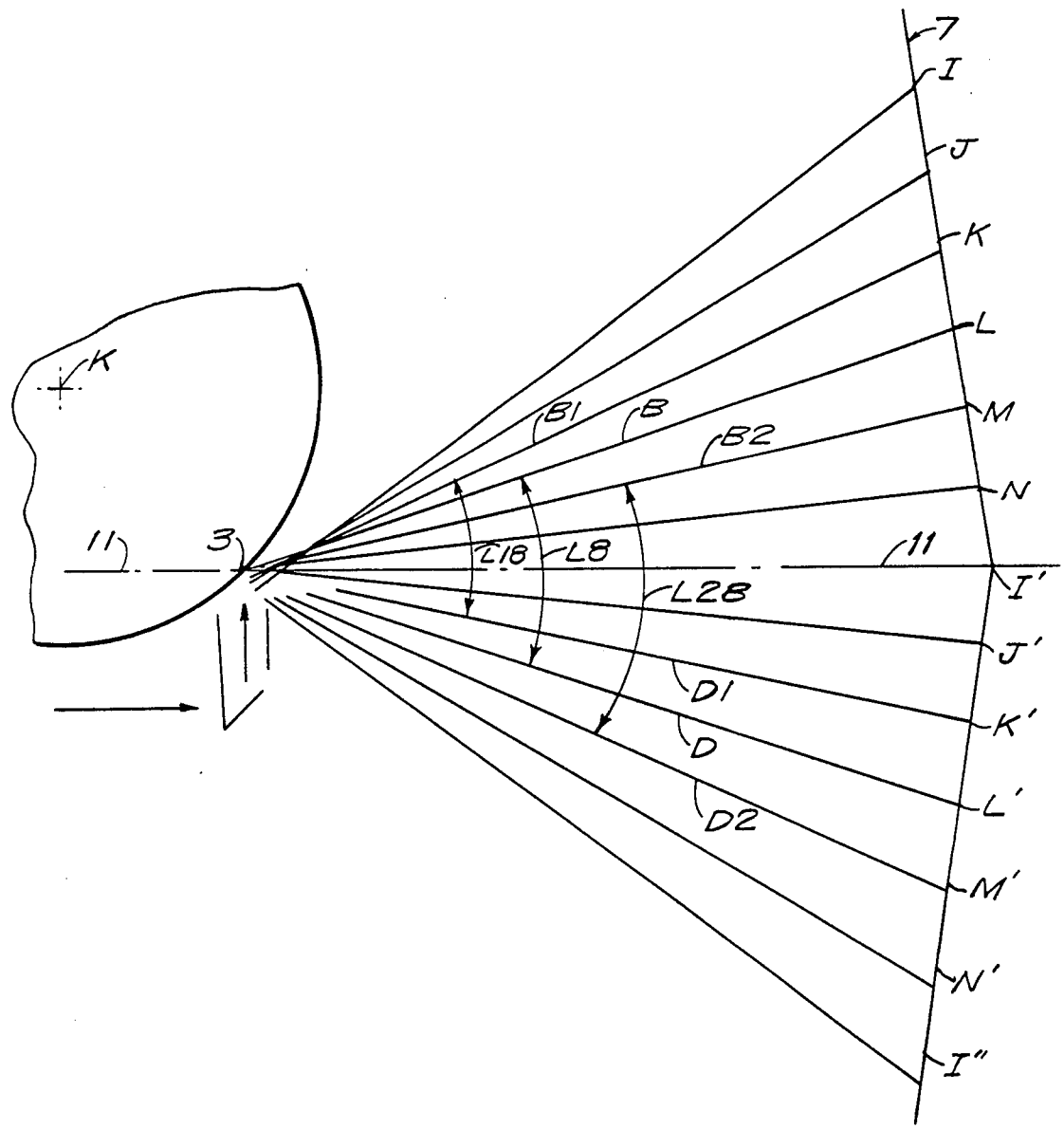
FIGS. 5 and 6 are diagrams illustrating that in embodiments of the present invention, unlike the prior art, the sweeping scanning angle continuously corresponds to one repeat length of the web.
Figure 6:
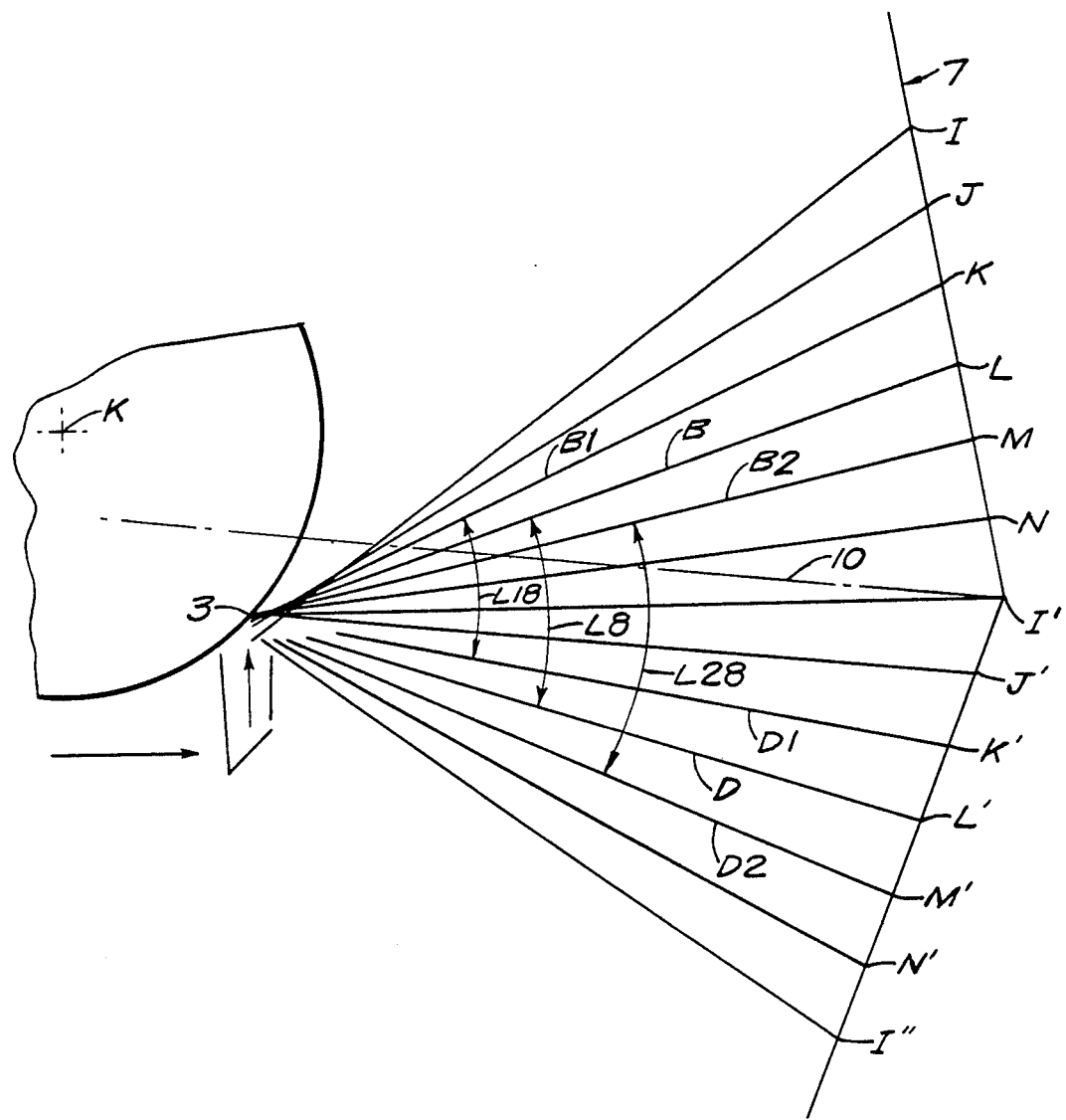

FIGS. 5 and 6 illustrate the relationships between the sweeping scanning angle and the corresponding images on the moving target web as they existed in prior art systems and as they exist in systems according to the present invention, respectively.

In both FIGS. 5 and 6 there is illustrated a target web 7 which comprises equidistant points I-J, J-K, K-L, L-M, M-N, N-I', I'-J', J'-K', K'-L', L'-M', M'-N', and N'-I". Points I and I', J and J', K and K', L and L', M and M', N and N', and I' and I" represent corresponding, i.e. repeating, points of a repeating web image. Thus, the web image repeat length for this embodiment is equal to any of the distances N-I', J-J', K-K', L-L', M-M', N-N', or I'-I".

Also illustrated in FIGS. 5 and 6 are scanning angle positions 8, 18, and 28 (hereinafter angles 8, 18 and 28, respectively). As is well known in the art, the number of degrees in such scanning angles is a function of the number of mirrored sides on the rotating prism. For 20 mirror prisms, the scanning angle necessarily measures 36°.

Referring first to FIG. 5, the points on the target web to which lines D and B of the scanning angle 8 are directed constitute the images provided to the viewer by the rotating prism mirrors 6a and 6b (shown previously). Thus, at one instant, the viewer will see the image on the target web at the end of sight line B and will simultaneously see the image on the target web at the end of the sight line D.

Generally, if the images at the ends of sight lines are identical, then a single, complete image will be presented to the viewer. However, if identical images are not present at the ends of the sight lines, then multiple or split images will be presented to the viewer.

Again with reference to FIG. 5, which depicts systems of the prior art where the target web 7 was centered on the viewing point 3, when the sweeping scanning angle is centered on the target web, as is shown by scanning angle 8, the images at the end of sight lines B and D are identical (being represented here by corresponding repeating web image points L and L') and therefore a single, substantially complete image would be presented to the viewer. However, when the scanning angle is not centered on the target web, as with angles 18 and 28 of FIG. 5, identical images are not present at the ends of the sight lines and split or multiple images would be presented to the viewer. Put another way, there is a mismatch between the images actually presented at the ends of the sight lines. For example, whereas a viewer would expect to see the matching images at points K and K' from the sight lines B1 and D1 of scanning angle 18, or the matching images at points M and M' from the sight lines B2 and D2 of scanning angle 28, neither the images at the end of sight lines B1 and D1 nor the images at the end of sight lines B2 and D2 present the matching images expected at points K and K' or M and M', respectively. Rather, the images at the ends of sight lines B1—D1 and B2—D2 are different, respectively, and are not the corresponding repeating images which are expected and thus a split or multiple image is presented to the viewer through either scanning position. In other words, the scanning angle does not correspond to the web repeat length in all viewing positions in systems of the prior art.

As illustrated in FIG. 6, this problem is eliminated in embodiments of the present invention because such embodiments maintain a correspondence between the scanning angle and the web repeat length throughout the viewing area of the web.

FIG. 6 shows an embodiment of the invention wherein the line 10 bisecting the target web 7 passes through the point midway between the center K of the drum and the viewing point 3. As is illustrated in FIG. 6, a single, complete image is presented to the viewer not only when the scanning angle is centered on the target web (as is scanning angle 8) but also when the scanning angle is not centered on the web (for example, as with scanning angles 18 and 28). With the present invention, the images at the end of sight lines B and D, B1 and D1, and B2 and D2 are the expected matching images at points L and L', K and K', and M and M', respectively. Thus, the present invention maintains a correspondence between the sweeping scanning angle and the web repeat length throughout the viewing area of the web by orienting the web as hereinbefore described.

Because of the rotation of the mirrors, the scanning angle 8, defined by lines B and D in FIGS. 5 and 6, is constantly sweeping in a clockwise direction. In the preferred embodiments of the present invention, even though D and B both sweep in the clockwise direction, the correspondence between the sweeping scanning angle and one repeat length of the target web is maintained.

It should be understood that the values disclosed in Table I and Table II in no way limit the scope of the invention and that there may be other embodiments within the scope of the invention, not shown here, in which the sweeping scanning angle approximately corresponds to one target web repeat length in all viewing positions so that the separation of image problem is lessened or eliminated.

What is claimed is:

1. An improved apparatus for inspecting successive impressions on a moving target web, comprising:
    (i) linear target support means,
    (ii) a rotatable member having a plurality of light reflecting surfaces successively presented by its rotary movement to receive and reflect successive light rays from the impressions on the moving target web during their movement throughout the observable pattern,
    (iii) means for rotating said rotatable member in time relation with the moving target web to produce a sweeping scanning angle whereby when the light rays reflected by the rotatable member are viewed, the impressions on the target web at the end of the sight lines which define the sweeping scanning angle will appear substantially stationary, and
    (iv) means for continuously maintaining exact correspondence of the sweeping scanning angle to one repeat length of the target web.

2. An improved apparatus for inspecting successive impressions on a moving target web, comprising:
    (i) linear target support means,
    (ii) a rotatable member having a plurality of light reflecting surfaces successively presented by its rotary movement to receive and reflect successive light rays from the impressions on the moving target web during their movement throughout the observable pattern,
    (iii) means for rotating said rotatable member in time relation with the moving target web to produce a sweeping scanning angle whereby when the light rays reflected by the rotatable member are viewed, the impressions on the target web at the end of the sight lines which define the sweeping scanning angle will appear substantially stationary, and
    (iv) means for continuously maintaining the sweeping scanning angle in exact correspondence to one repeat length of the target web in small incremental regions along the target web surrounding the points where the sight lines defining said sweeping scanning angle intercept the target web when the sweeping scanning angle is centered on the target web.

3. Apparatus for inspecting successive impressions on a moving target web as claimed in claim 1, wherein a line passing through a point approximately halfway between the center of the rotary drum prism and the viewing point bisects the target area of said linear web support means.

4. Apparatus for inspecting successive impressions on a moving target web as claimed in claim 2, wherein a line passing through a point approximately halfway between the center of the rotary drum prism and the viewing point bisects the target area of said linear web support means.

5. Apparatus for inspecting successive impressions on a target web as claimed in claim 1, wherein said linear target web support means comprises two separate sections which form an obtuse angle with each other which is bisected by said line passing through a point approximately halfway between the center of the rotary prism and the viewing point.

6. Apparatus for inspecting successive impressions on a moving target web as claimed in claim 5 wherein said bisecting line is substantially parallel to the horizontal line which intersects said rotary prism viewing point and the point directly opposite said rotary prism viewing point on said linear web support means.

7. Apparatus for inspecting successive impressions on a moving target web as claimed in claim 5, wherein said bisecting line is substantially non-parallel to the horizontal line which intersects said rotary prism viewing point and the point directly opposite said rotary prism viewing point on said linear web support means.

8. Apparatus for inspecting successive impressions on a target web, as claimed in claim 2, wherein said target area of said linear target web support means is straight.

9. A method for inspecting successive impressions on a moving target web comprising:
(i) rotating, in time relation with the moving target web, a rotatable member having a plurality of light reflecting surfaces, successively presented by its rotary movement to receive and reflect impressions from said moving target web during its movement throughout the observable pattern, so that a sweeping scanning angle is produced whereby when the light rays reflected by the rotatable member are viewed, the impressions on said target web at the end of the sight lines which define the sweeping scanning angle will appear substantially stationary; and
(ii) maintaining the target web in such an orientation with respect to the rotatable member that there will be continuous exact correspondence of the sweeping scanning angle to one repeat length of the target web.

* * * * *